United States Patent [19]

Saito et al.

[11] 4,048,222

[45] Sept. 13, 1977

[54] PROCESS FOR PREPARING TRANS-4-AMINOMETHYL-CYCLOHEXANE-1-CARBOXYLIC ACID

[75] Inventors: Tsuyoshi Saito; Kiro Asano, both of Tokyo, Japan

[73] Assignee: Kureha Kagaku Kogyo Kabushiki Kaisha, Tokyo, Japan

[21] Appl. No.: 447,794

[22] Filed: Mar. 4, 1974

[51] Int. Cl.² .................................... C07C 99/00
[52] U.S. Cl. .................................... 260/514 J
[58] Field of Search ................... 260/514 J, 514 CA

[56] References Cited

U.S. PATENT DOCUMENTS

| | | | |
|---|---|---|---|
| 3,499,925 | 3/1970 | Naito et al. | 260/514 |
| 3,932,497 | 1/1976 | Fukumi et al. | 260/514 |

FOREIGN PATENT DOCUMENTS

| | | | |
|---|---|---|---|
| 2,349,056 | 4/1974 | Germany | 260/468 |
| 4,532,258 | 10/1970 | Japan | 260/514 |
| 4,727,506 | 7/1972 | Japan | 260/514 |
| 1,202,189 | 8/1970 | United Kingdom | 260/514 |
| 1,112,897 | 5/1968 | United Kingdom | 260/514 |

OTHER PUBLICATIONS

Grossins, Unit Processes in Organic Synthesis, pp. 578–579 (1958).

*Primary Examiner*—Robert Gerstl
*Attorney, Agent, or Firm*—Sughrue, Rothwell, Mion, Zinn and Macpeak

[57] ABSTRACT

A process for preparing trans-4-aminomethylcyclohexane-1-carboxylic acid which comprises catalytically reducing p-aminomethylbenzoic acid or a derivative thereof in the presence of a ruthenium catalyst in a solution of a strong acid or a strong alkali as a solvent is disclosed.

10 Claims, No Drawings

PROCESS FOR PREPARING TRANS-4-AMINOMETHYL-CYCLOHEXANE-1-CARBOXYLIC ACID

BACKGROUND OF THE INVENTION

1. Field of the Invention

This invention relates to a process for preparing trans-4-aminomethylcyclohexane-1-carboxylic acid in high yield in a single step from p-aminomethylbenzoic acid or a derivative thereof by a simultaneous reduction and trans-isomerization.

2. Description of the Prior Art

Trans-4-aminomethylcyclohexane-1-carboxylic acid has been recently recognized as a valuable raw material for producing a wide variety of pharmaceuticals or high molecular weight materials. A typical conventional process for producing trans-4-aminomethylcyclohexane-1-carboxylic acid generally comprises two steps, i.e., catalytically reducing p-aminomethylbenzoic acid or a derivative thereof or cyanobenzoic acid or a derivative thereof to produce the cis isomer of 4-aminomethylcyclohexane-1-carboxylic acid, and converting the resulting cis isomer of the carboxylic acid into the desired trans isomer by heating the cis isomer in an aqueous solution of an acid or alkali.

SUMMARY OF THE INVENTION

An object of this invention is to provide a process for preparing trans-4-aminomethylcyclohexane-1-carboxylic acid which substantially eliminates the disadvantages associated with known processes and which is suitable for the production of this carboxylic acid on an industrial scale.

DETAILED DESCRIPTION OF THE INVENTION

According to the process of this invention, the reduction and trans-isomerization steps which are carried out in separate steps in the conventional process can be effected simultaneously in a single step and, further, the desired 4-aminomethylcyclohexane-1-carboxylic acid can be prepared in high yield over the yield attainable in the conventional two-step procedure.

That is, the process in accordance with the present invention comprises catalytically reducing and trans-isomerizing p-aminomethylbenzoic acid or a derivative thereof in the presence of a ruthenium catalyst and a solution of a strong acid or a strong alkali as a solvent at a temperature in the range of from about 70° to about 200° C under a hydrogen pressure of 20 to 200 kg/cm$^2$ for a period of 0.5 to 20 hours.

One of the characteristic features of the present invention is to use a ruthenium catalyst. The present inventors previously found that a ruthenium catalyst can effectively be used in the reduction of p-aminomethylbenzoic acid as disclosed in British Patent Specification No. 1,202,189. As a result of further studies by the present inventors, it was found that the ruthenium catalyst is superior to other known catalysts in the reduction and the trans-isomerization of p-aminomethylbenozoic acid in the presence of a strong acid or a strong alkali according to the process of this invention. Thus, the ruthenium catalyst used in the present invention functions as a reduction and trans-isomerization catalyst for p-aminomethylbenzoic acid or a derivative thereof in the presence of a solution of a strong acid or a strong alkali.

The ruthenium catalyst used in the present invention can be in the form of ruthenium metal or a ruthenium oxide which is optionally supported on an appropriate carrier which is conventionally used as a carrier for catalysts, for example, activated carbon, barium sulfate, calcium carbonate, alumina, diatomaceous earth, thorium oxide or the like. Other suitable carriers can also be used in the present invention for supporting the ruthenium catalyst. The amount of the ruthenium catalyst is not critical, but it is preferred to use the ruthenium catalyst in an amount of from 0.2 to 15% by weight calculated as ruthenium metal based on the weight of the reactant, p-aminomethylbenzoic acid or a derivative thereof.

As is apparent to one skilled in the art, the amount of catalyst will vary depending upon the manner of reaction, i.e., whether a batch type reaction or a continuous process as is described hereinafter in greater detail. In the batch type reaction, the amount of the catalyst is preferably in the range of from 0.3 to 5.0% by weight calculated as ruthenium metal based on the weight of the reactant from the standpoint of economy. However, the amount of the catalyst in the batch type reaction can range from 0.2 to 15% by weight, without adversely affecting the reaction of the invention.

The term "p-aminomethylbenzoic acid or a derivative thereof" used throughout the specification and claims of this invention includes the compounds represented by the formula

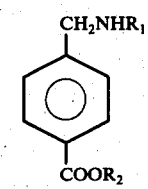

wherein $R_1$ represents a hydrogen atom or an acetyl group, and $R_2$ represents a hydrogen atom, a lower alkyl group having 1 to 6 carbon atoms or a cyclohexyl group. Typical examples of the compounds represented by the above formula are p-aminomethylbenzoic acid, methyl p-aminomethylbenzoate, 4-N-acetylaminomethylbenzoic acid, methyl 4-N-acetylaminomethylbenzoate and the like.

Another feature of the present invention is to use a specific solvent which can be a solution of either a strong acid or a strong alkali. Examples of strong acids which can be used in the process of this invention are inorganic acids such as hydrochloric acid, sulfuric acid, phosphoric acid and the like and organic acids such as formic acid, acetic acid and the like, or a mixture thereof. Examples of the strong alkalis which can be used in the present invention are alkali metal or alkaline earth metal hydroxides such as sodium hydroxide, potassium hydroxide, barium hydroxide, calcium hydroxide and the like or a mixture thereof. The solvent for the solution of a strong acid or an alkali can be water or a lower alkanol having 1 to 4 carbon atoms such as methanol, ethanol, propanol or butanol.

The concentration of the strong acid in the solution as a solvent varies depending upon the type of acid used. For example, hydrochloric acid having a concentration of from one normal (1N) to 20 normal (20N) can preferably be used in the process of this invention. The strong alkali can preferably be used as a solution having a concentration of from 5% to 20% by weight.

In addition to the above acid or alkali solution as a solvent, organic solvents which are generally used in organic reactions can effectively be used to increase the solubility of the starting material, p-aminomethylbenzoic acid and a derivative thereof. Generally speaking, the organic solvents should preferably be those which are capable of dissolving the reactant to an extent of at least 1% by weight. Also, it is necessary that the organic solvents used do not undergo hydrogenation and/or decomposition under reaction conditions and it is necessary that the solvents be inert to the above acid or alkali as well as the catalyst, e.g., the solvent must not poison the catalyst. Suitable examples of organic solvents are dioxane, lower alkanols having 1 to 6 carbon atoms such as methanol, ethanol, propanol, butanol, pentanol, hexanol and the like.

The starting material is preferably used at a concentration of from 5 to 50% by weight in the above solvent or solvent mixture.

The process of this invention is generally carried out under a hydrogen pressure of from about 20 to about 200 kg/cm² (gauge), preferably 50 to 150 kg/cm² (gauge), at a temperature of from about 70° to about 200° C, preferably 80 to 150° C. At a temperature higher than about 200° C, the deamination of the reactant and the product tends to occur. The initial hydrogen pressure is not critical so long as it falls within the above range, but it is preferably adjusted in such a manner that the final hydrogen pressure at the end of the reaction be still above 20 kg/cm² (gauge) at room temperature.

The reaction of this invention is effected until the hydrogen uptake reaches equilibrium, and the time required for the completion of the process of this invention slightly varies with the reaction conditions as described above, but is generally from 0.5 to 20 hours.

Both the yield of the desired trans-4-aminomethylcyclohexane-1-carboxylic acid and the isomerization ratio, i.e., the conversion ratio of the cis isomer into the trans isomer obtainable by the process of this invention are extremely high and no disadvantages or inferior aspects can be found in the process of this invention as compared with the conventional twostep process. Thus, the process of this invention is of great value in the industrial production of trans-4-aminomethylcyclohexane-1-carboxylic acid from p-aminomethylbenzoic acid.

As described above, the reduction and trans-isomerization process of this invention can be carried out in either batch manner or continuous manner. For example, the former process can conveniently be carried out using a pressure-resistant vessel such as an autoclave and the latter process can conveniently be carried out by continuously feeding the solution of reactant and hydrogen gas into one end of a tubular reactor over the catalyst placed in the reactor while continuously recovering the product from the other end of the reactor. The reaction conditions such as the proportion of the catalyst relative to the reactants, the type of solvent and the concentration of acid or alkali in the solvent, the reaction temperature, the hydrogen pressure and the like are essentially the same in both the batch process and the continuous process. In the continuous process, the retention time of the reactant in the reactor varies depending upon the type of the reactor, feeding rate of the reactant, reaction temperature, type of the acid or alkali used and other parameters and can easily be determined experimentally by measuring the time required for reaching equilibrium in the hydrogen uptake with respect to the specific reaction conditions employed.

When a solution of an alkali is used as a reaction solvent in the process of this invention, the product is obtained in the form of an alkali metal or alkaline earth metal salt, the metal being that of the alkali used, and the salt thus obtained can then be converted into the free carboxylic acid using any well known procedure, for example, by treating the salt with an ion-exchange resin.

The present invention is further illustrated in greater detail by reference to the following examples, but they are not to be construed as limiting the scope of this invention. Unless otherwise indicated all parts, percents and ratios are by weight.

EXAMPLE 1

30 g of p-aminomethylbenzoic acid was reduced in 300 ml of each of the solvents and in the presence of the specific catalyst as shown in Table 1. The reduction was carried out under an initial hydrogen pressure of 100 kg/cm² at a temperature of 150° C until the hydrogen uptake reached equilibrium in each instance. The results obtained are shown in Table 1 where Run Nos. 3 to 6 are given for comparative purposes.

Table 1

| Run No. | Catalyst | Solvent | | | | | |
|---|---|---|---|---|---|---|---|
| | | NaOH (20% 99. soln.) | | HCl (14N) | | 10% KOCH₃(EtOH)[2] | |
| | | Yield (%)[3] | Trans/Cis[4] | Yield (%) | Trans/Cis | Yield (%) | Trans/Cis |
| 1 | 5% Ru-C (3g) | 73 | 78/22 | 91 | 89/11 | 81 | 81/19 |
| 2 | 5% RuO₂ (3g) | 78 | 75/25 | 90 | 90/10 | 83 | 83/17 |
| 3 | 5% Pt-C (3G) | 30 | 15/85 | 70 | 21/79 | 10 | 20/80 |
| 4 | 5% Pt-Rh-C[1] (3g) | 29 | 13/87 | 65 | 18/82 | 10 | 21/79 |
| 5 | 5% Pd-C (3g) | Trace | — | Trace | — | Trace | — |
| 6 | Raney Nickel | Trace | — | Trace | — | Trace | — |

[1]Pt:Rh = 1:1 by weight
[2]Potassium alcoholate
[3]Yield of 4-aminomethylcyclohexane-1-carboxylic acid including the trans and cis isomers
[4]Weight ratio As is apparent from the results shown in Table 1, the process of this invention is far superior to the conventional process using a platnium, platinum-rhodium, palladium or Raney nickel catalyst with respect to the yield of 4-aminomethylcyclohexane-1-carboxylic acid and the isomerization ratio.

EXAMPLE 2

Trans-4-aminomethylcyclohexane-1-carboxylic acid was prepared using 30 g of p-aminomethylbenzoic acid, 3 g of 5% ruthenium supported on activated carbon and 300 ml of 14N hydrochloric acid or a 20% aqueous sodium hydroxide solution as a solvent under the conditions shown in Table 2 below. For the purposes of comparison, the results obtained by isomerizing 100% cis-4-aminomethylcyclohexane-1-carboxylic acid under the same conditions as above but without using hydrogen for reduction are also shown in Table 2.

Table 2

| Solvent | Reduction of p-Amino-methylbenzoic Acid | | Isomerization of Cis-4-Aminomethyl-cyclohexane-1-Carboxylic Acid | |
|---|---|---|---|---|
| | HCl (14N) | NaOH (20%) | HCl (14N) | NaOH (20%) |
| Temperature (° C) | 150 | 150 | 150 | 150 |
| $H_2$ Pressure (kg/cm$^2$) | 100 | 100 | — | — |
| Time (hour) | 10 | 15 | 10 | 15 |
| Yield (%) | 88 | 75 | — | — |
| Ratio of Trans/Cis | 89/11 | 78/22 | 53/47 | 43/57 |

*Aqueous solution, by weight.

The results shown in Table 2 clearly indicate that the reduction-isomerization process of this invention is superior with respect to isomerization of cis-4-aminomethylcyclohexane-1-carboxylic acid.

EXAMPLE 3

Trans-4-aminomethylcyclohexane-1-carboxylic acid was prepared using 30 g of p-aminomethylbenzoic acid, 3 g of a 5% ruthenium supported on activated carbon and hydrochloric acid having the concentration shown in Table 3 below at a temperature of 80° C, 100° C, 150° C and 180° C under an initial hydrogen pressure of 150 kg/cm$^2$. The results obtained are shown in Table 3 below.

Table 3

| Concentration of HCl (Normality) | Temperature (° C) | | | | | | | |
|---|---|---|---|---|---|---|---|---|
| | 80 | | 100 | | 150 | | 180 | |
| | Yield (%) | Trans/Cis | Yield (%) | Trans/Cis | Yield (%) | Trans/Cis | Yield (%) | Trans/Cis |
| 0 | 85 | 10/90 | 84 | 10/90 | 70 | 15/85 | 60 | 16/84 |
| 6 | 87 | 20/80 | 87 | 35/65 | 82 | 43/57 | 80 | 62/38 |
| 12 | 95 | 40/60 | 91 | 50/50 | 90 | 65/35 | 82 | 69/31 |
| 14 | 94 | 45/55 | 93 | 50/50 | 91 | 90/10 | 81 | 82/18 |

As is apparent from the results shown in Table 3, the isomerization, i.e., the conversion of the cis isomer into the trans isomer proceeds slightly even in the absence of the acid as the temperature used in the process increases. Also, the maximum yield of the desired product and the maximum degree of isomerization are achieved at a temperature near 150° C and rather tend to decrease at a higher temperature (180° C).

EXAMPLE 4

30 g of p-aminomethylbenzoic acid, 3 g of 5% ruthenium supported on activated carbon and 100 ml of an aqueous sodium hydroxide solution as a solvent under the conditions shown in Table 4 below were charged in an autoclave and then reacted at a temperature of 80° C, 100° C, and 150° C, respectively, under an initial hydrogen pressure of 150 kg/cm$^2$ to obtain trans-4-aminomethylcyclohexane-1-carboxylic acid in each case. The reaction product thus obtained was in the form of the sodium salt and was converted into the free acid using an ion-exchange resin.

The quantitative determination of each of the cis and trans isomers of the product was conducted by gas chromatography of samples which were obtained by esterifying the reaction product.

Table 4

| Concentration of Sodium Hydroxide Molar Ratio of Raw Material*/ Sodium Hydroxide wt% | Temperature (° C) | | | | | |
|---|---|---|---|---|---|---|
| | 80 | | 100 | | 150 | |
| | Yield (%) | Trans/Cis | Yield (%) | Trans/Cis | Yield (%) | Trans/Cis |
| NaOH 5 % (Molar Ratio: 0.625) | 93 | 70/30 | 90 | 75/25 | 78 | 73/27 |
| NaOH 8 % (Molar Ratio: 1.0) | 95 | 80/20 | 93 | 82/18 | 79 | 81/19 |
| NaOH 10 % (Molar Ratio: 1.25) | 95 | 80/20 | 92 | 82/18 | 77 | 80/20 |

*p-Aminomethylbenzoic Acid

As is apparent from the results shown in Table 4, extremely excellent results can be obtained even in the presence of sodium hydroxide, with particularly excellent results being obtained at temperatures of about 80° C to 100° C.

The isomerization of the cis isomer into the trans isomer has hitherto been conducted at a high temperature, however, the isomerization according to the present invention can be achieved at a low temperature with good results being obtained.

EXAMPLE 5

In a pressure resistant (resistant to 300 kg/cm$^2$) tubular reactor having an inside diameter of 1 inch was packed a 10 wt% ruthenium supported on a flaked carbon carrier in a length of 2 m. An aqueous sodium hydroxide solution containing p-aminomethylbenzoic acid (concentration of raw material: 10 wt%; molar ratio of raw material/NaOH: 1.0) was passed continuously through the above catalyst bed at a rate of 10 l/hr at a temperature of 90° C under a hydrogen pressure of 100 kg/cm$^2$ for 10 hours to reduce the p-aminomethylbenzoic acid. The results obtained are shown in Table 5 below.

Table 5

| | |
|---|---|
| Yield (based on the raw material containing both cis and trans isomers) | 70 % |
| Unreacted Products | 20 % |
| By-products | 10 % |
| Trans/Cis Ratio | 70 : 30 |

EXAMPLE 6

The same procedure as described in Example 4 was conducted except that Ba(OH)$_2$ or Ca(OH)$_2$ was used as the strong alkali. The results obtained are shown in Table 6 below.

Table 6

| | (Reaction Temperature: 100° C, Hydrogen Pressure: 100 kg/cm²) | |
|---|---|---|
| | Ba(OH)₂ | Ca(OH)₂ |
| Molar Ratio of Raw Material/Alkali | 0.5 | 0.5 |
| Yield (based on the raw material containing both cis and trans isomers) | 95 % | 95 % |
| Trans/Cis | 70/30 | 63/37 |

While the invention has been described in detail with reference to the specific embodiments thereof, it is apparent to one skilled in the art that various modifications and changes can be made therein without departing from the spirit and scope thereof.

What is claimed is:

1. A process for preparing trans-4-aminomethylcyclohexane-1-carboxylic acid which comprises simultaneously reducing and trans-isomerizing, for 0.5 to 20 hours, at a pressure of 20-200 Kg/cm², at a temperature of 70°-200° C, in the presence of a ruthenium catalyst, 5-50% by weight of solvent of p-aminomethylbenzoic acid or a derivative thereof in an aqueous solution or an alkanol solution of a strong acid selected from the group consisting of hydrochloric acid, sulfuric acid, phosphoric acid, formic acid, acetic acid and mixtures thereof as a solvent, said alkanol having 1 to 6 carbon atoms.

2. The process according to claim 1, wherein said p-aminomethylbenzoic acid or a derivative thereof is a compound represented by the formula

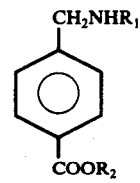

wherein $R_1$ represents a hydrogen atom or an acetyl group, and $R_2$ represents a hydrogen atom, a lower alkyl group having 1 to 6 carbon atoms or a cyclohexyl group.

3. The process according to claim 2, wherein said compound is methyl p-aminomethylbenzoate.

4. The process according to claim 2, wherein said compound is 4-N-acetylaminomethylbenzoic acid.

5. The process according to claim 2, wherein said compound is methyl 4-N-acetylaminomethylbenzoate.

6. The process according to claim 1, wherein said ruthenium catalyst is ruthenium metal or a ruthenium oxide.

7. The process according to claim 1, wherein said aqueous solution or said alkanol solution additionally contains another organic solvent selected from the group consisting of dioxane and alkanols having 1 to 6 carbon atoms.

8. The process according to claim 6, wherein said ruthenium catalyst is supported on activated carbon, barium sulfate, calcium carbonate, alumina, diatomaceous earth or thorium oxide.

9. The process according to claim 1, wherein said reducing and trans-isomerizing is in a batch manner.

10. The process according to claim 1, wherein said reducing and trans-isomerizing is in a continuous manner.

* * * * *